(12) United States Patent
Brettschneider et al.

(10) Patent No.: US 7,837,767 B2
(45) Date of Patent: Nov. 23, 2010

(54) PROCESSES FOR REMOVING ORGANIC COMPONENTS FROM GASES CONTAINING HYDROGEN CHLORIDE

(75) Inventors: Ole Brettschneider, Berlin (DE); Knud Werner, Krefeld (DE)

(73) Assignee: Bayer MaterialScience AG, Leverkusen (DE)

( * ) Notice: Subject to any disclaimer, the term of this patent is extended or adjusted under 35 U.S.C. 154(b) by 274 days.

(21) Appl. No.: 12/110,419

(22) Filed: Apr. 28, 2008

(65) Prior Publication Data
US 2008/0264253 A1  Oct. 30, 2008

(30) Foreign Application Priority Data
Apr. 26, 2007  (DE) .................. 10 2007 020 144

(51) Int. Cl.
*B01D 53/00* (2006.01)
*C01B 7/04* (2006.01)

(52) U.S. Cl. .............................. 95/142; 95/143; 95/148; 62/617

(58) Field of Classification Search .......... 95/141–148; 62/600, 602, 617; 423/210, 245.1; 203/41
See application file for complete search history.

(56) References Cited

U.S. PATENT DOCUMENTS

| | | | |
|---|---|---|---|
| 4,774,070 A | 9/1988 | Itoh et al. | |
| 4,846,852 A * | 7/1989 | Schweitzer et al. | 95/125 |
| 5,137,548 A * | 8/1992 | Grenier et al. | 95/41 |
| 5,345,771 A * | 9/1994 | Dinsmore | 62/641 |
| 5,611,840 A * | 3/1997 | Kraus et al. | 95/41 |
| 5,740,682 A | 4/1998 | Lavie et al. | |
| 6,793,905 B1 * | 9/2004 | Buttner et al. | 423/488 |
| 7,294,173 B2 * | 11/2007 | Masetto et al. | 95/148 |
| 2006/0123842 A1 * | 6/2006 | Sohn et al. | 62/617 |
| 2007/0261437 A1 * | 11/2007 | Boonstra et al. | 62/617 |
| 2007/0277551 A1 * | 12/2007 | Kamper | 62/617 |
| 2008/0295688 A1 * | 12/2008 | Sesing et al. | 95/93 |

FOREIGN PATENT DOCUMENTS

| | | |
|---|---|---|
| DE | 19534448 | 3/1997 |
| EP | 0233773 A1 | 8/1987 |
| EP | 1801089 | 6/2007 |
| EP | 1894885 | 3/2008 |
| WO | WO-2006/038705 | 4/2006 |
| WO | WO-2006/137583 | 12/2006 |

* cited by examiner

*Primary Examiner*—Frank M Lawrence
(74) *Attorney, Agent, or Firm*—Connolly Bove Lodge & Hutz LLP

(57) ABSTRACT

Processes comprising: providing a crude gas stream having a temperature not exceeding 40° C., the crude gas stream comprising hydrogen chloride and at least one organic impurity; condensing at least a portion of the at least one organic impurity from the crude gas stream at a temperature not exceeding 0° C. to form a prepurified gas stream and a condensate comprising condensed organic impurity; subjecting at least a portion of the prepurified gas stream to adsorption on an adsorption medium to provide a purified gas stream; and separating the condensate into at least a head gas stream comprising residual hydrogen chloride and a sump stream comprising at least a portion of the condensed organic impurity.

30 Claims, 1 Drawing Sheet

PROCESSES FOR REMOVING ORGANIC COMPONENTS FROM GASES CONTAINING HYDROGEN CHLORIDE

BACKGROUND OF THE INVENTION

Adsorptive separation to remove contaminants from gas streams, particularly organic contaminants, is frequently used in chemical processing.

As adsorbents are used, they periodically require regeneration. During regeneration of an adsorbent, the adsorbent is conventionally heated and brought into contact with a regenerating gas stream. The adsorbed components thereby dissolve in the regenerating gas stream and the adsorbent is unloaded.

A process for the catalytic oxidation of HCl gas is described in European Patent No. EP 233 773 B1, in which a HCl gas contaminated with organic impurities such as benzene, chlorobenzene and the like is prepurified for use in a Deacon process (catalytic HCl oxidation by means of oxygen). In the prepurification described therein, activated carbon is used as the adsorber and is regenerated after use. It is further proposed to regenerate the adsorber at elevated temperatures or under reduced pressure and optionally using an inert gas.

Depending on the organic load of the gas stream that is to be purified and on the vapor pressure of the organic components that are to be separated off, the use of a low-temperature condensation provided upstream of the adsorption process can be economically advantageous in some instances. In such processes, a major part of the organic load can be separated off in a condensation system, while after-purification to the required purities can take place with the aid of an adsorption step.

Such a combination of condensation and adsorption is described, for example, in U.S. Pat. No. 5,740,682. As discussed therein, for example, hydrocarbons are removed from air.

However, in a process for removing organic components from HCl gas streams, the above-described combination of low-temperature condensation and subsequent adsorption may result in a significant amount of HCl and phosgene which may be present in the gas stream being dissolved in the organic components separated off by the condensation. The dissolution of those components would then give rise to significant subsequent costs for the conversion of phosgene and HCl into sodium chloride and sodium carbonate via sodium hydroxide. At the same time, the amounts of phosgene and HCl discharged from such a process would represent a not inconsiderable chlorine loss, which is undesirable in particular in a process with a chlorine circuit.

BRIEF SUMMARY OF THE INVENTION

The invention relates, in general, to processes for working up hydrogen-chloride-containing gas streams, which are contaminated with one or more organic compounds, through a combination of condensation and adsorption.

Various preferred embodiments of the present invention relate, in particular, to the purification of hydrogen-chloride-containing process gases from isocyanate preparation.

Various embodiments of the processes according to the present invention can provide an improved separation process which permits the removal and optionally the re-use of organic components from a crude gas containing HCl.

Additionally, various embodiments of the processes according to the present invention can reduce the loss of valuable HCl-constituents such as chlorine in the process gas purification of hydrogen-chloride-containing gas streams contaminated with organic compounds.

One embodiment of a process according to the present invention includes a process comprising: providing a crude gas stream having a temperature not exceeding 40° C., the crude gas stream comprising hydrogen chloride and at least one organic impurity; condensing at least a portion of the at least one organic impurity from the crude gas stream at a temperature not exceeding 0° C. to form a prepurified gas stream and a condensate comprising condensed organic impurity; subjecting at least a portion of the prepurified gas stream to adsorption on an adsorption medium to provide a purified gas stream; and separating the condensate into at least a head gas stream comprising residual hydrogen chloride and a sump stream comprising at least a portion of the condensed organic impurity.

Thus, in one embodiment, the present invention includes a process for removing organic components from a hydrogen-chloride-containing crude gas stream, which may optionally be hot, comprising the steps: A) adjustment of the crude gas stream that is to be purified to a temperature not exceeding 40° C.; B) condensation of at least some of the organic components of the crude gas stream at a temperature not exceeding 0° C., preferably not exceeding −10° C.; C) at least partial adsorption of the residual organic components that remain in the prepurified gas stream after the condensation, on an adsorption medium; D) provision of the purified gas stream; characterized in that the condensate obtained under B) is subjected to a rectification F); and optional subsequent heat exchange between the gas stream leaving the adsorption C) and the crude gas stream entering the process.

BRIEF DESCRIPTION OF THE SEVERAL VIEWS OF THE DRAWING

The foregoing summary, as well as the following detailed description of the invention, may be better understood when read in conjunction with the appended drawing. For the purpose of assisting in the explanation of the invention, there is shown in the drawing a representative embodiment which is considered illustrative. It should be understood, however, that the invention is not limited in any manner to the precise arrangements and instrumentalities shown.

In the drawing.

DETAILED DESCRIPTION OF THE INVENTION

Figure 1:
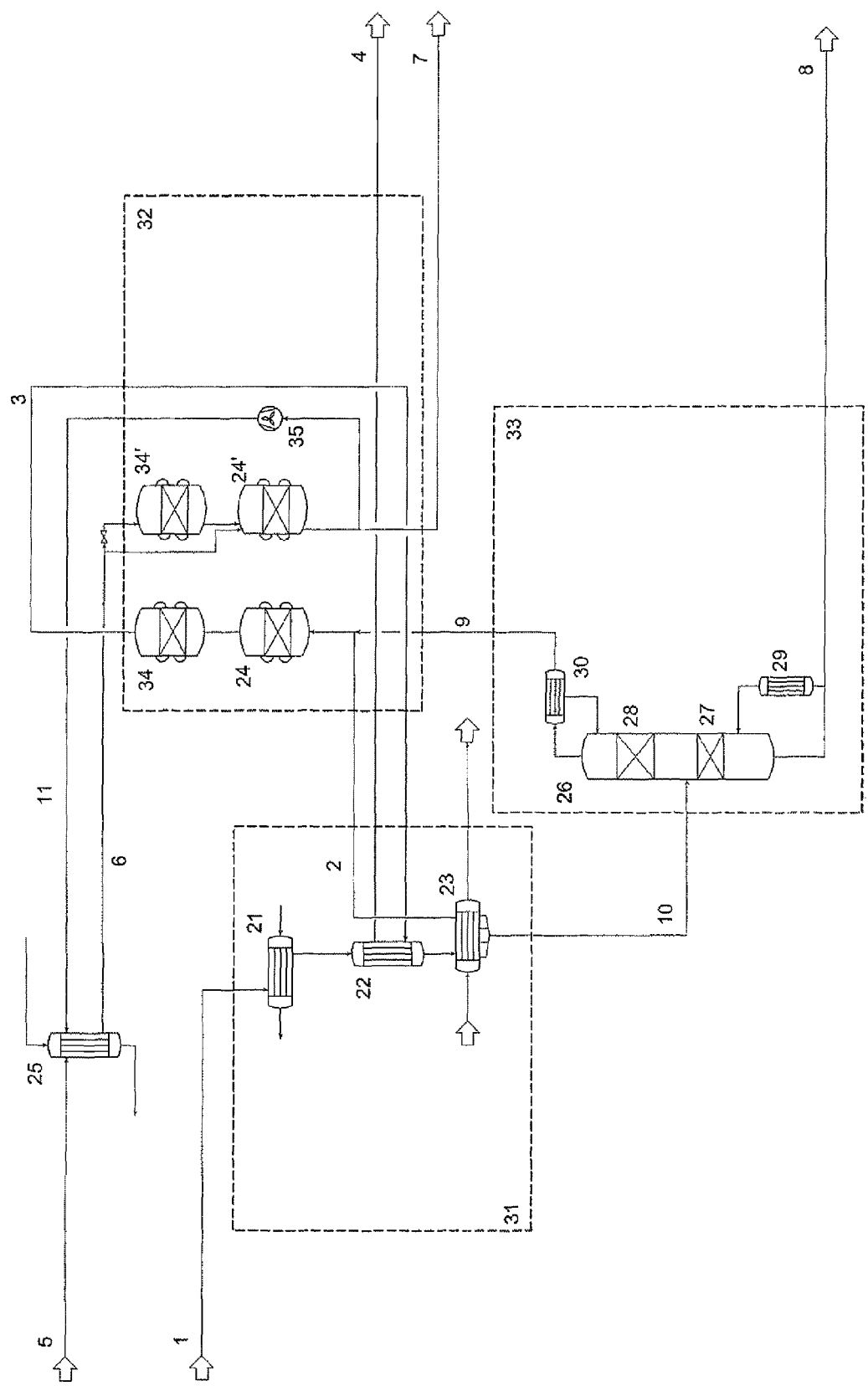
FIG. 1 is a flow diagram of a process of crude gas purification according to one embodiment of the present invention.

As used herein, the singular terms "a" and "the" are synonymous and used interchangeably with "one or more" and "at least one," unless the language and/or context clearly indicates otherwise. Accordingly, for example, reference to "a gas stream" herein or in the appended claims can refer to a single gas stream or more than one gas stream. Additionally, all numerical values, unless otherwise specifically noted, are understood to be modified by the word "about."

Suitable adsorption agents which can be used in an adsorption in accordance with the various embodiments of processes according to the present invention include, but are not limited to, activated carbon, zeolites, aluminum oxide, bentonite, silica gel and/or organometallic complexes. Activated carbon is preferred. Suitable types of apparatus for the production of an intensive gas-adsorbent contact are simple fixed beds, fluid beds, fluidized beds, or fixed beds movable as a whole.

Advantages of the adsorptive removal of components from gas streams include very high purities of the purified gas stream that can be achieved, and that, in the case of regenerative adsorption processes, it is possible to recover the organic components for targeted disposal or for returning to preceding preparation processes.

Crude gas streams containing hydrogen chloride for use in the various embodiments of the processes according to the present invention preferably include a waste stream containing hydrogen chloride which is obtained as by-product in one of the following processes, for example: isocyanate preparation from phosgene and amines, acid chloride preparation, polycarbonate preparation, the preparation of vinyl chloride from ethylene dichloride, and the chlorination of aromatic compounds.

The temperature of an initial crude gas stream can be, in particular, up to 400° C., preferably up to 250° C., particularly preferably up to 150° C. A crude gas stream can be provided for use in the various embodiments of the processes according to the present invention by cooling an initial crude gas stream.

Preference is given to various processes which are characterized by the cooling of a crude gas stream, first in a cooler to a temperature not exceeding 45° C. Also preferably, cooling of an initial crude gas stream can take place in a second step, in particular in a recuperator, to a temperature not exceeding 40° C. In various particularly preferred embodiments of the processes according to the invention, heat exchange between the gas stream leaving the adsorption and the crude gas stream entering the process can take place in a recuperator. Cooling preferably takes place in a first step in a cooler to a temperature not exceeding 45° C. and in a second step in a recuperator to a temperature not exceeding 40° C.

Various preferred embodiments of the processes according to the invention include regeneration of the adsorption medium, wherein the adsorption medium is regenerated with the aid of a further inert gas stream which is heated, in particular to a temperature of at least 50° C.

In various preferred embodiments of the processes according to the invention, the rectification F) can take place at a temperature in the sump evaporator of at least 40° C., preferably at least 60° C.

The processes according to the various embodiments of the present invention are particularly preferably used when the crude gas stream that is to be purified consists substantially of hydrogen chloride and optionally up to 2 wt. % phosgene. As used herein, "consists essentially of" with respect to hydrogen chloride content in the crude gas stream refers to a hydrogen chloride content of at least 80% by weight, more preferably at least 90% by weight, and most preferably at least 95% by weight.

Organic components that can be separated from a crude gas stream in accordance with the various embodiments of the processes according to the present invention preferably include hydrocarbons and/or halogenated hydrocarbons, particularly preferably aromatic hydrocarbons such as benzene, toluene, xylenes and $C_6$-$C_{12}$-aliphatic compounds, or chlorinated hydrocarbons such as carbon tetrachloride, vinyl chloride and dichloroethane, or chlorinated aromatic hydrocarbons such as chlorobenzene, hexachlorobenzene or orthodichlorobenzene.

In various particularly preferred embodiments of the processes according to the invention, at least a portion of the head gas stream obtained in the rectification is subjected to the adsorption together with the prepurified gas stream.

In various particularly preferred embodiments of the processes according to the invention, the adsorption can take place in at least two adsorption stages. Particularly preferably, the adsorption medium of the first stage in C) is regenerated with the aid of a partial stream of the crude gas stream, and the loaded crude gas partial stream is optionally combined with the crude gas stream entering the condensation B).

A preferred modification of the various embodiments of the processes according to the invention includes regeneration of the adsorbent, wherein the adsorption medium of the first stage of the adsorption C) is regenerated from time to time, alternately with the crude gas partial stream, by means of an inert gas in a single pass.

The processes according to the invention are particularly preferably used when the hydrogen-chloride-containing purified gas stream is used further in a production process for the preparation of chlorine from hydrogen chloride and oxygen, in particular in a catalyzed gas-phase oxidation of hydrogen chloride with oxygen or in a non-thermal reaction of hydrogen chloride and oxygen. Coupling with the catalyzed gas-phase oxidation of hydrogen chloride with oxygen (Deacon process) is particularly preferred.

As already described above, the catalytic process known as the Deacon process is preferably used in combination with the process according to the invention. In that process, hydrogen chloride is oxidized to chlorine with oxygen in an exothermic equilibrium reaction, with the formation of steam. The reaction temperature is conventionally from 150 to 500° C. and the conventional reaction pressure is from 1 to 25 bar. Because the reaction is an equilibrium reaction, it is advantageous to work at the lowest possible temperatures at which the catalyst still has sufficient activity. It is also advantageous to use oxygen in over-stoichiometric amounts relative to the hydrogen chloride. A two- to four-fold oxygen excess, for example, is conventional. Because there is no risk of losses of selectivity, it can be economically advantageous to work at a relatively high pressure and accordingly with a longer residence time as compared with normal pressure.

Suitable preferred catalysts for the Deacon process comprise ruthenium oxide, ruthenium chloride or other ruthenium compounds on silicon dioxide, aluminum oxide, titanium dioxide or zirconium dioxide as support. Suitable catalysts can be obtained, for example, by applying ruthenium chloride to the support and then drying or drying and calcining. In addition to or instead of a ruthenium compound, suitable catalysts can also comprise compounds of other noble metals, for example gold, palladium, platinum, osmium, iridium, silver, copper or rhenium. Suitable catalysts can further comprise chromium(III) oxide.

The catalytic hydrogen chloride oxidation can be carried out adiabatically or, preferably, isothermally or approximately isothermally, discontinuously, but preferably continuously as a fluid or fixed bed process, preferably as a fixed bed process, particularly preferably in tubular reactors on heterogeneous catalysts at a reactor temperature of from 180 to 500° C., preferably from 200 to 400° C., particularly preferably from 220 to 350° C., and a pressure of from 1 to 25 bar (from 1000 to 25,000 hPa), preferably from 1.2 to 20 bar, particularly preferably from 1.5 to 17 bar and especially from 2.0 to 15 bar.

Conventional reaction apparatuses in which the catalytic hydrogen chloride oxidation is carried out are fixed bed or fluidized bed reactors. The catalytic hydrogen chloride oxidation can preferably also be carried out in a plurality of stages.

In the case of the adiabatic, isothermal or approximately isothermal procedure, it is also possible to use a plurality of reactors, that is to say from 2 to 10, preferably from 2 to 6, particularly preferably from 2 to 5, especially 2 or 3 reactors, connected in series with intermediate cooling. The hydrogen chloride can either be added in its entirety, together with the oxygen, upstream of the first reactor, or distributed over the various reactors. This series connection of individual reactors can also be combined in one apparatus.

In a further preferred form of a device suitable for the process there is used a structured bulk catalyst in which the catalytic activity increases in the direction of flow. Such structuring of the bulk catalyst can be effected by variable impregnation of the catalyst support with active substance or by variable dilution of the catalyst with an inert material. As the inert material there can be used, for example, rings, cylinders or spheres of titanium dioxide, zirconium dioxide or mixtures thereof, aluminum oxide, steatite, ceramics, glass, graphite, stainless steel and/or nickel alloys. When catalyst shaped bodies are used, as is preferred, the inert material should preferably have similar outside dimensions.

Suitable catalyst shaped bodies are shaped bodies of any shape, preferred shapes being lozenges, rings, cylinders, stars, cart wheels or spheres and particularly preferred shapes being rings, cylinders or star-shaped extrudates.

Suitable heterogeneous catalysts are in particular ruthenium compounds or copper compounds on support materials, which can also be doped, with preference being given to optionally doped ruthenium catalysts. Examples of suitable support materials are silicon dioxide, graphite, titanium dioxide of rutile or anatase structure, zirconium dioxide, aluminum oxide or mixtures thereof, preferably titanium dioxide, zirconium dioxide, aluminum oxide or mixtures thereof; particularly preferably γ- or δ-aluminum oxide or mixtures thereof.

The copper or ruthenium supported catalysts can be obtained, for example, by impregnating the support material with aqueous solutions of $CuCl_2$ or $RuCl_3$ and optionally of a promoter for doping, preferably in the form of their chlorides. Shaping of the catalyst can take place after or, preferably, before the impregnation of the support material.

Suitable promoters for the doping of the catalysts are alkali metals such as lithium, sodium, potassium, rubidium and cesium, preferably lithium, sodium and potassium, particularly preferably potassium, alkaline earth metals such as magnesium, calcium, strontium and barium, preferably magnesium and calcium, particularly preferably magnesium, rare earth metals such as scandium, yttrium, lanthanum, cerium, praseodymium and neodymium, preferably scandium, yttrium, lanthanum and cerium, particularly preferably lanthanum and cerium, or mixtures thereof.

The shaped bodies can then be dried and optionally calcined at a temperature of from 100 to 400° C., preferably from 100 to 300° C., for example, under a nitrogen, argon or air atmosphere. The shaped bodies are preferably first dried at from 100 to 150° C. and then calcined at from 200 to 400° C.

The hydrogen chloride conversion in a single pass can preferably be limited to from 15 to 90%, preferably from 40 to 85%, particularly preferably from 50 to 70%. After separation, some or all of the unreacted hydrogen chloride can be fed back into the catalytic hydrogen chloride oxidation. The volume ratio of hydrogen chloride to oxygen at the entrance to the reactor is preferably from 1:1 to 20:1, preferably from 1:1 to 8:1, particularly preferably from 1:1 to 5:1.

The heat of reaction of the catalytic hydrogen chloride oxidation can advantageously be used to produce high-pressure steam. This can be used to operate a phosgenation reactor and/or distillation columns, in particular isocyanate distillation columns.

In a further step, the chlorine that has formed is separated off. The separation step conventionally comprises a plurality of stages, namely the separation and optional recycling of unreacted hydrogen chloride from the product gas stream of the hydrogen chloride oxidation, drying of the resulting stream containing substantially chlorine and oxygen, and the separation of chlorine from the dried stream.

The separation of unreacted hydrogen chloride and of steam that has formed can be carried out by removing aqueous hydrochloric acid from the product gas stream of the hydrogen chloride oxidation by cooling. Hydrogen chloride can also be absorbed in dilute hydrochloric acid or water.

The invention will now be described in further detail with reference to the following non-limiting example.

Example

Referring to FIG. 1, in a first stage 31, an initial crude gas stream 1 is precooled in a cooler 21 and passed through the recuperator 22 to provide a crude gas stream having a temperature below 10° C. In this example, the initial crude gas stream comprised a hydrogen chloride gas from a TDI production. Organic impurities such as chlorobenzene, hexachlorobenzene and/or orthodichlorobenzene are partly condensed in the condenser 23 at a temperature of −35° C. and conveyed away as stream 10 (condensate). At the same time, HCl and optionally phosgene are dissolved in the condensate as already described above.

In a second stage 32, the prepurified crude gas stream 2 is passed over an adsorber bed 24 where organic impurities are further reduced.

The loaded adsorber bed 24', which is operated alternately with the adsorber bed 24, is purified (regenerated) with an inert gas 6 which is composed of fresh inert gas 5 and a return stream 11 and is preheated in the heat exchanger 25. The return stream 11 is conveyed with a blower 35.

After passing through the adsorber 24', the loaded regenerating gas stream 7 can be worked up (not shown).

After passing through the adsorber 24, the gas passes over a redundant adsorber system 34, 34' of activated carbon. In this redundant adsorber system, one adsorber 34 is always available for adsorption, while the redundant adsorber 34' can be regenerated. The regeneration can be carried out either with hot inert gas, or with hot crude gas or with inert gas in a circulating stream (neither of which is shown in FIG. 1).

After purification by adsorption in the second stage of the process gas stream 3 passes through the recuperator 22 from the first stage 31 of the process thereby exchanging heat with the crude gas stream 1 and can be made available as stream 4 to the following Deacon-process where it is oxidized to chlorine (not shown in FIG. 1). Stage 31 and stage 32 of the process embodiment depicted are carried out isobarically at a pressure of 6 bar, except for the apparatus and pipe pressure losses.

The condensate 10 obtained in the first stage 31 of the process is fed to a third stage 33 of the process (rectification). In the embodiment shown in FIG. 1, the third stage of the process includes a rectification column 26 having a concentrating section 28, a stripping section 27, as well as a sump evaporator 29 and a head condenser 30. The condensate 10 from stage 31, which is loaded inter alia with HCl and phosgene, is fed to the rectification column 26 in stage 33 between the stripping section 27 and the concentrating section 28. In the stripping section 27, the vapor generated in the sump evaporator 29 rises upwards countercurrently to the organic stream flowing down through the column 26. The proportion of HCl and phosgene in the rising vapor stream is thereby continuously increased. HCl and phosgene are at the same time removed from the liquid running down. In the concentrating section 28 of the column, further concentration of HCl and phosgene in the gas stream takes place, while the organic components are depleted. The HCl/phosgene concentration or the organic concentration at the head of the column or downstream of the head condenser 30 of the column is influenced substantially by the condenser temperature and the column reflux produced thereby. The head condenser 30 is in the form of a dephlegmator, so that a gaseous vapor stream 9 (head gas stream) containing substantially phosgene and HCl is removed via the head of the rectification and is passed, together with the prepurified gas stream 2, to the adsorption of stage 32 of the process. The condensation temperature of the rectification is to be so chosen that the organic load in the stream 9 is only a fraction of the organic load present in stream 1. The condenser temperature is −10° C.

The organic stream 8 (sump stream) removed at the sump of the column is free of HCl and phosgene to the greatest possible extent and is made available for further processing or disposal. The sump temperature is 140° C. The column pressure is above the pressure level of stage 32 of the process. Stream 9 can thus be passed into the adsorption of the second process stage without being compressed.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A process comprising:
   providing a crude gas stream having a temperature not exceeding 40° C., the crude gas stream comprising hydrogen chloride and at least one organic impurity;
   condensing at least a portion of the at least one organic impurity from the crude gas stream at a temperature not exceeding 0° C. to form a prepurified gas stream and a condensate comprising condensed organic impurity;
   subjecting at least a portion of the prepurified gas stream to adsorption on a first adsorption medium to provide a purified gas stream;
   separating the condensate into at least a head gas stream comprising residual hydrogen chloride and a sump stream comprising at least a portion of the condensed organic impurity, and combining at least a portion of the head gas stream with the prepurified gas stream prior to adsorption.

2. The process according to claim 1, further comprising heat exchange between the purified gas stream and the crude gas stream.

3. The process according to claim 2, wherein the heat exchange is carried out in a recuperator.

4. The process according to claim 1, wherein the crude gas stream is condensed at a temperature not exceeding −10° C.

5. The process according to claim 1, wherein providing the crude gas stream having a temperature not exceeding 40° C. comprises providing an initial crude gas stream having a temperature exceeding 40° C. and cooling the initial crude gas stream to the temperature not exceeding 40° C.

6. The process according to claim 2, wherein the crude gas stream is condensed at a temperature not exceeding −10° C.

7. The process according to claim 2, wherein providing the crude gas stream having a temperature not exceeding 40° C. comprises providing an initial crude gas stream having a temperature exceeding 40° C. and cooling the initial crude gas stream to the temperature not exceeding 40° C.

8. The process according to claim 5, wherein cooling the initial crude gas stream to the temperature not exceeding 40° C. comprises a first temperature adjustment carried out in a cooler to a temperature not exceeding 45° C. and a second temperature adjustment carried out in a recuperator to the temperature not exceeding 40° C.

9. The process according to claim 8, wherein the second temperature adjustment comprises heat exchange between the purified gas stream and the initial crude gas stream leaving the first temperature adjustment.

10. The process according to claim 1, wherein the process is carried out at a pressure of up to 20 bar.

11. The process according to claim 2, wherein the process is carried out at a pressure of up to 20 bar.

12. The process according to claim 1, wherein the process is carried out at a pressure of 2 to 12 bar.

13. The process according to claim 1, wherein separating the condensate comprises feeding the condensate to a rectifying column in a rectification stage.

14. The process according to claim 2, wherein separating the condensate comprises feeding the condensate to a rectifying column in a rectification stage.

15. The process according to claim 13, wherein the rectification stage further comprises a sump evaporator operating at a temperature of at least 40° C.

16. The process according to claim 13, wherein the rectification stage further comprises a sump evaporator operating at a temperature of at least 100° C.

17. The process according to claim 1, further comprising regenerating the first adsorption medium, wherein regenerating comprises contacting the first adsorption medium with a heated inert gas stream.

18. The process according to claim 2, further comprising regenerating the first adsorption medium, wherein regenerating comprises contacting the first adsorption medium with a heated inert gas stream.

19. The process according to claim 1, wherein the crude gas stream comprises hydrogen chloride in an amount of at least 80% by weight, and further comprises phosgene in an amount of up to 2% by weight.

20. The process according to claim 2, wherein the crude gas stream comprises hydrogen chloride in an amount of at least 80% by weight, and further comprises phosgene in an amount of up to 2% by weight.

21. The process according to claim 1, wherein the at least one organic impurity comprises a component selected from the group consisting of hydrocarbons, halogenated hydrocarbons and mixtures thereof.

22. The process according to claim 2, wherein the at least one organic impurity comprises a component selected from the group consisting of hydrocarbons, halogenated hydrocarbons and mixtures thereof.

23. The process according to claim 1, wherein the at least one organic impurity comprises a component selected from the group consisting of benzene, toluene, xylenes, $C_6$-$C_{12}$-aliphatic compounds, carbon tetrachloride, vinyl chloride, dichloroethane, chlorobenzene, hexachlorobenzene, orthodichlorobenzene, and mixtures thereof.

24. The process according to claim 2, wherein the at least one organic impurity comprises a component selected from the group consisting of benzene, toluene, xylenes, $C_6$-$C_{12}$-aliphatic compounds, carbon tetrachloride, vinyl chloride, dichloroethane, chlorobenzene, hexachlorobenzene, orthodichlorobenzene, and mixtures thereof.

25. The process according to claim 1, wherein the adsorption is carried out in at least two adsorption stages.

26. The process according to claim 2, wherein the adsorption is carried out in at least two adsorption stages.

27. The process according to claim 1, wherein the crude gas stream comprises hydrogen chloride in an amount of at least 80% by weight, and further comprises phosgene, and wherein the purified gas stream is fed to a process for the production of chlorine from hydrogen chloride and oxygen.

28. The process according to claim 2, wherein the crude gas stream comprises hydrogen chloride in an amount of at least 80% by weight, and further comprises phosgene, and wherein the purified gas stream is fed to a process for the production of chlorine from hydrogen chloride and oxygen.

29. The process according to claim 1, wherein the crude gas stream comprises a hydrogen-chloride-containing waste stream obtained from a process selected from the group consisting of isocyanate preparation from phosgene and amines, acid chloride preparation, polycarbonate preparation, preparation of vinyl chloride from ethylene dichloride, chlorination of aromatic compounds, and combinations thereof.

30. The process according to claim 2, wherein the crude gas stream comprises a hydrogen-chloride-containing waste stream obtained from a process selected from the group consisting of isocyanate preparation from phosgene and amines, acid chloride preparation, polycarbonate preparation, preparation of vinyl chloride from ethylene dichloride, chlorination of aromatic compounds, and combinations thereof.

* * * * *